United States Patent
Kabaya et al.

(10) Patent No.: US 8,292,883 B2
(45) Date of Patent: Oct. 23, 2012

(54) ELECTROSURGICAL APPARATUS AND METHOD OF CONTROLLING ELECTROSURGICAL APPARATUS

(75) Inventors: Akinori Kabaya, Hachioji (JP); Takashi Mihori, Akiruno (JP)

(73) Assignee: Olympus Medical Systems Corp., Tokyo (JP)

( * ) Notice: Subject to any disclaimer, the term of this patent is extended or adjusted under 35 U.S.C. 154(b) by 1043 days.

(21) Appl. No.: 12/252,054

(22) Filed: Oct. 15, 2008

(65) Prior Publication Data

US 2010/0094282 A1    Apr. 15, 2010

(51) Int. Cl.
*A61B 18/04* (2006.01)
*A61B 18/18* (2006.01)

(52) U.S. Cl. ............... 606/34; 606/29; 606/50; 606/51; 606/42

(58) Field of Classification Search .............. 606/29, 606/50, 51, 42
See application file for complete search history.

(56) References Cited

U.S. PATENT DOCUMENTS

| | | | |
|---|---|---|---|
| 5,438,302 A | 8/1995 | Goble | |
| 2002/0022836 A1 | 2/2002 | Goble et al. | |
| 2002/0052599 A1 | 5/2002 | Goble | |
| 2007/0129726 A1 | 6/2007 | Eder et al. | |
| 2007/0276363 A1* | 11/2007 | Patton et al. | 606/51 |
| 2008/0172052 A1* | 7/2008 | Eder et al. | 606/50 |
| 2009/0048595 A1 | 2/2009 | Mihori et al. | |
| 2009/0234351 A1 | 9/2009 | Desinger et al. | |
| 2011/0077630 A1* | 3/2011 | Tanaka et al. | 606/29 |

FOREIGN PATENT DOCUMENTS

| | | |
|---|---|---|
| EP | 1 080 694 A1 | 3/2001 |
| EP | 2 025 297 A2 | 2/2009 |
| JP | 05-337129 | 12/1993 |
| JP | 08-229050 | 9/1996 |
| JP | 8-512229 | 12/1996 |
| JP | 2001-029356 | 2/2001 |
| JP | 2002-502660 | 1/2002 |
| JP | 2002-537938 | 11/2002 |
| JP | 2004-512135 | 4/2004 |
| JP | 2007-203088 | 8/2007 |
| JP | 2008-036439 | 2/2008 |
| JP | 2008-510507 | 4/2008 |
| JP | 2009-045456 | 3/2009 |
| WO | 95/02369 | 1/1995 |
| WO | WO 99/40857 | 8/1999 |

(Continued)

OTHER PUBLICATIONS

International Search Report dated Dec. 22, 2009.
Extended Supplementary European Search Report dated Feb. 27, 2012 issued in counterpart European Patent Application No. 09817859.3.

*Primary Examiner* — Nicholas Lucchesi
*Assistant Examiner* — Ian Holloway
(74) *Attorney, Agent, or Firm* — Scully, Scott, Murphy & Presser, P.C.

(57) ABSTRACT

An electrosurgical apparatus in the present invention has a high frequency power generation section which generates high frequency power to be applied to a living tissue, a voltage detection section which detects the voltage of the high frequency power, a current detection section which detects the current of the high frequency power, an impedance computation section which computes the impedance of the living tissue on the basis of the voltage and the current, and a control section which, when the impedance exceeds a predetermined threshold value, performs control for increasing the frequency of the high frequency power stepwise on the high frequency power generation section.

10 Claims, 4 Drawing Sheets

FOREIGN PATENT DOCUMENTS

| | | |
|---|---|---|
| WO | 00/53112 A2 | 9/2000 |
| WO | 02/36028 A1 | 5/2002 |
| WO | 2006/021550 A1 | 3/2006 |
| WO | WO 2008/142404 A1 | 11/2008 |

* cited by examiner

ELECTROSURGICAL APPARATUS AND METHOD OF CONTROLLING ELECTROSURGICAL APPARATUS

BACKGROUND OF THE INVENTION

1. Field of the Invention

The present invention relates to an electrosurgical apparatus and a method of controlling the electrosurgical apparatus and, more particularly to an electrosurgical apparatus capable of performing a treatment on a living tissue by high frequency electric power and a method of controlling the electrosurgical apparatus.

2. Description of the Related Art

Conventionally, an electrosurgical apparatus such as a cautery knife is used to perform a treatment such as dissection, coagulation or hemostasis on a living tissue in a surgical operation or the like. Such an electrosurgical apparatus is configured by being provided with a high frequency power supply which outputs high frequency electric power, and a treatment instrument connected to the high frequency power supply.

It is known that in a case where coagulation or hemostasis on a living tissue for example is performed by using the electrosurgical apparatus configured as described above, the state of dehydration of an objective portion and the state of joining in the objective portion relate closely to each other. That is, if the state of dehydration of the objective portion is closer to the completely dehydrated state, the reliability of joining state in the objective portion is higher.

For example, an apparatus proposed in Japanese Patent Application Laid-Open Publication No. 2008-36439 is widely known as an apparatus having a configuration similar to that of the above-described electrosurgical apparatus.

SUMMARY OF THE INVENTION

An electrosurgical apparatus in the present invention includes a high frequency power generation section which generates high frequency power to be applied to a living tissue, a voltage detection section which detects the voltage of the high frequency power, a current detection section which detects the current of the high frequency power, an impedance computation section which computes the impedance between holding members for grasping the living tissue, on the basis of the voltage and the current, and a control section which, when the impedance exceeds a predetermined threshold value, performs control for increasing the frequency of the high frequency power stepwise on the high frequency power generation section.

A method of controlling an electrosurgical apparatus in the present invention includes a step of generating high frequency power to be applied to a living tissue, a step of detecting the voltage of the high frequency power, a step of detecting the current of the high frequency power, a step of computing the impedance between holding members for grasping the living tissue, on the basis of the voltage and the current, and a step of perfotiuing control for increasing the frequency of the high frequency power stepwise when the impedance exceeds a predetermined threshold value.

DETAILED DESCRIPTION OF PREFERRED EMBODIMENTS

An embodiment of the present invention will be described with reference to the accompanying drawings.

Figure 1:
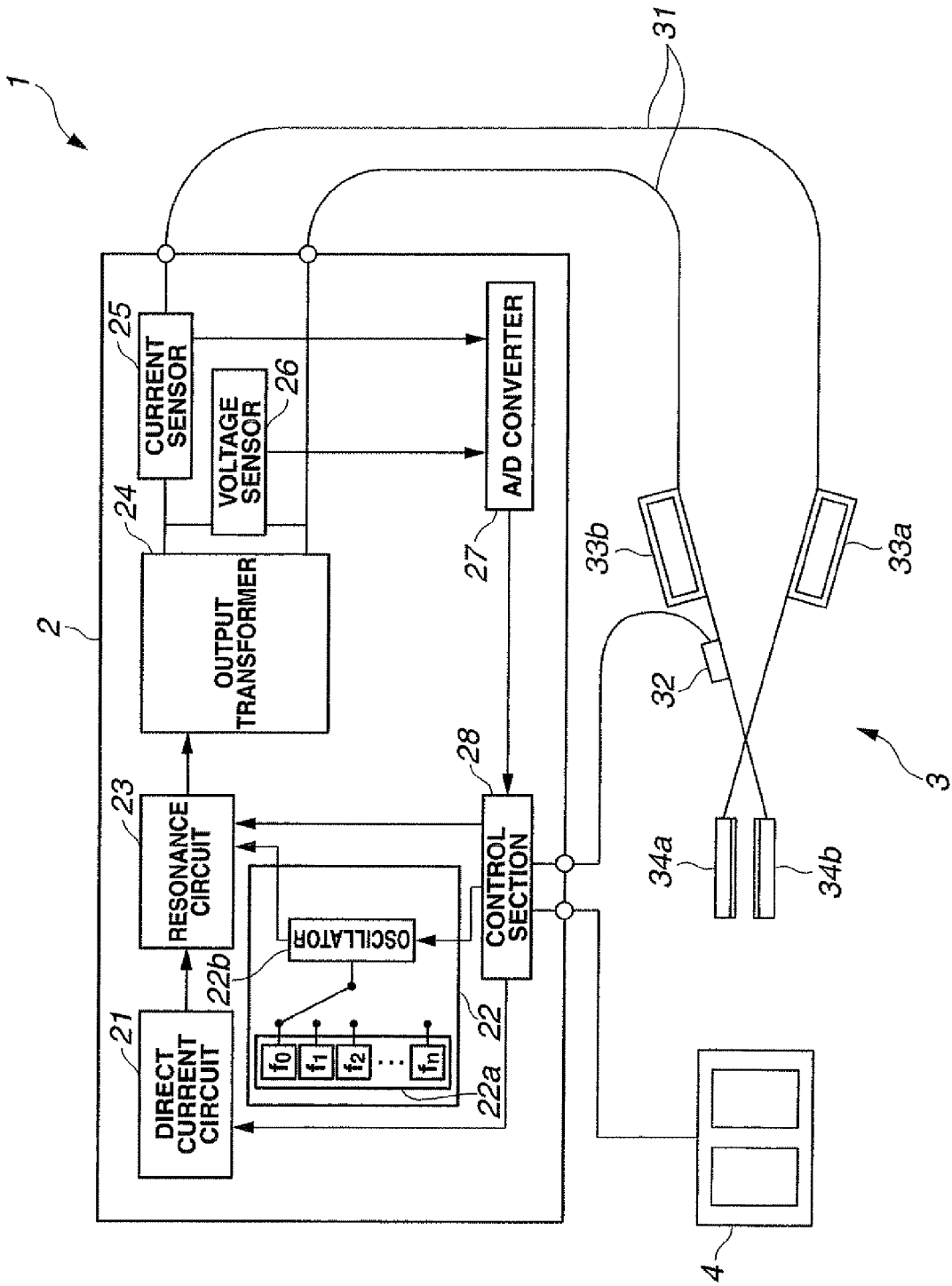
FIG. 1 is a diagram showing the configuration of an essential portion of an electrosurgical apparatus according to an embodiment of the present invention.
Figure 2:
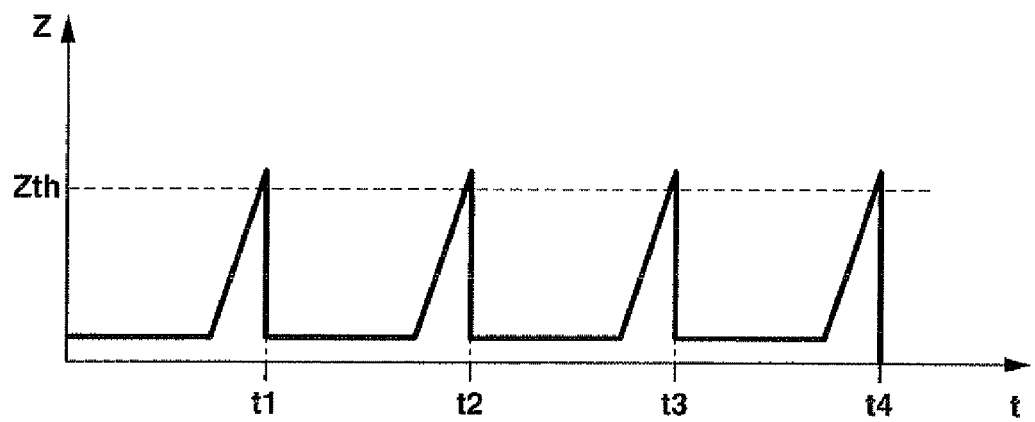
FIG. 2 is a diagram showing changes with respect to time in the value of impedance of a living tissue.
Figure 3:
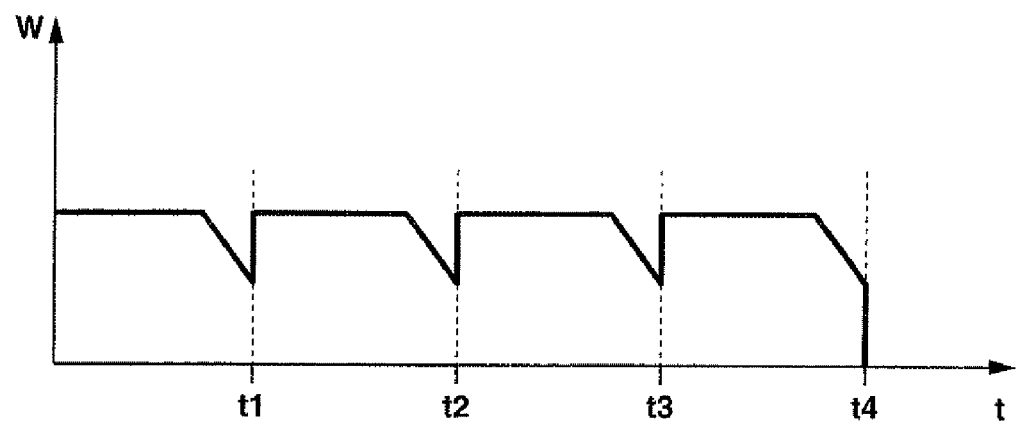
FIG. 3 is a diagram showing changes with respect to time in the value of electric power applied to the living tissue.
Figure 4:
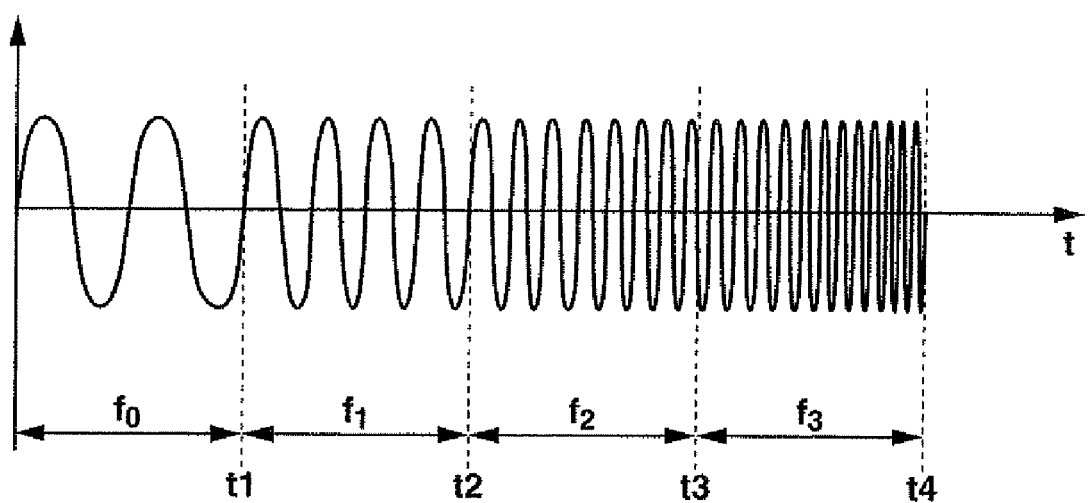
FIG. 4 is a diagram showing a state where the frequency of high frequency power applied to the living tissue changes stepwise.
Figure 5:
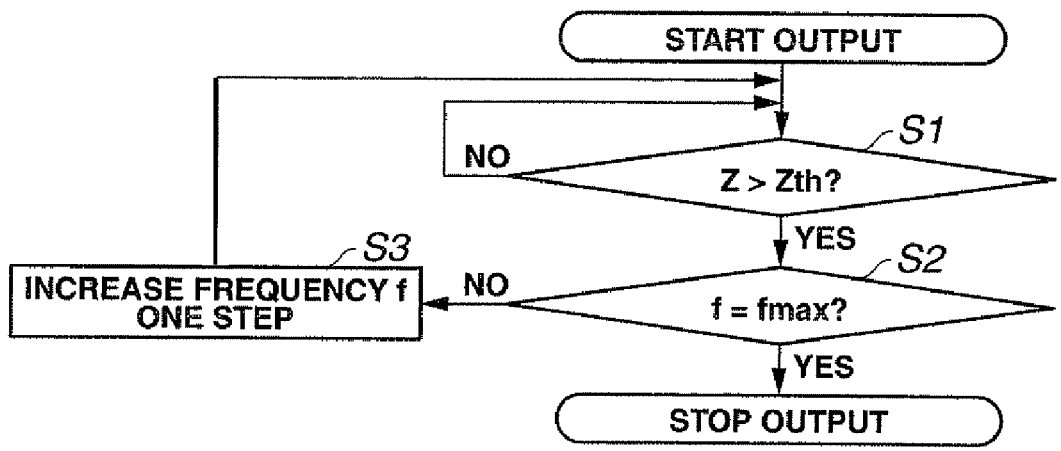
FIG. 5 is a diagram showing an example of processing performed in the electrosurgical apparatus shown in FIG. 1.
Figure 6:
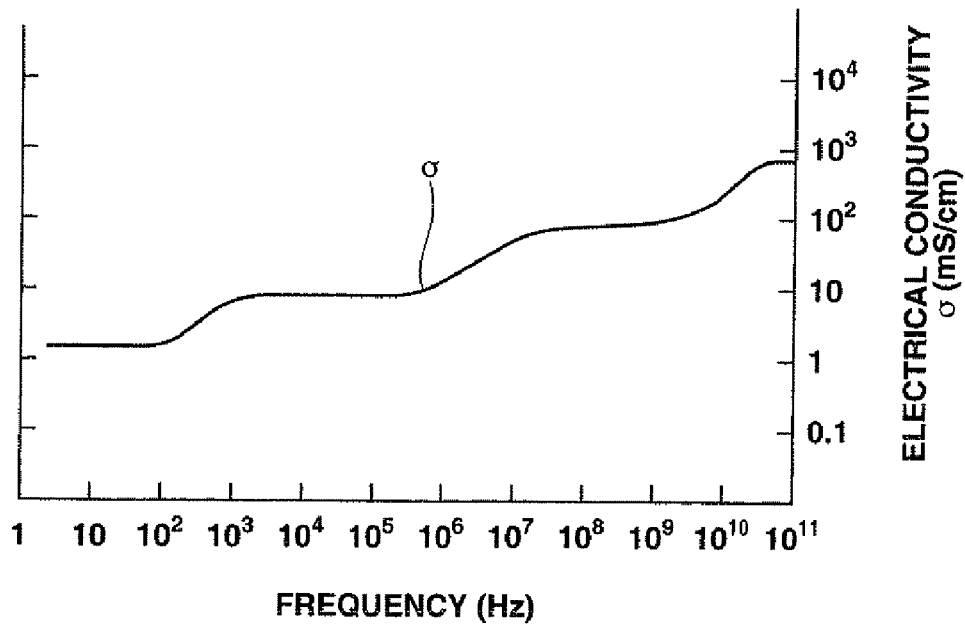
FIG. 6 is a diagram showing the correlation between the frequency and the electric conductivity of the living tissue.

FIGS. 1 to 6 relate to an embodiment of the present invention. FIG. 1 is a diagram showing the configuration of an essential portion of an electrosurgical apparatus according to the embodiment of the present invention. FIG. 2 is a diagram showing changes with respect to time in the value of impedance of a living tissue. FIG. 3 is a diagram showing changes with respect to time in the value of electric power applied to the living tissue. FIG. 4 is a diagram showing a state where the frequency of high frequency power applied to the living tissue changes stepwise. FIG. 5 is a diagram showing an example of processing performed in the electrosurgical apparatus shown in FIG. 1. FIG. 6 is a diagram showing the correlation between the frequency and the electric conductivity of the living tissue.

As shown in FIG. 1, an electrosurgical apparatus 1 is configured to have a high frequency power supply 2 which outputs high frequency power, and a treatment instrument 3 which can be connected to the high frequency power supply 2 via a cable 31, and with which a treatment on a living tissue 101 is performed by supplying to the living tissue 101 high frequency power outputted from the high frequency power supply 2. A foot switch 4 provided as an operation command section for supplying a command to the high frequency power supply 2 is also connected to the high frequency power supply 2.

The treatment instrument 3 is provided with a hand switch 32 for outputting a command signal for outputting high frequency power from the high frequency power supply 2. For example, the hand switch 32 outputs the command signal only during a time period during which the switch is pressed by the action of an operator's hand or the like.

The foot switch 4 has such a configuration as to output a command signal for outputting high frequency power from the high frequency power supply 2. For example, the foot switch 4 outputs the command signal only during a time period during which the switch is pressed by the action of an operator's foot or the like.

The high frequency power supply 2 is configured to have a direct current power supply circuit 21, a waveform generation circuit 22, a resonance circuit 23, an output transformer 24, a current sensor 25, a voltage sensor 26, an A/D converter 27, and a control section 28.

The direct current power supply circuit 21 converts power supplied from a commercial power supply or the like not shown in the figure into direct current power having a signal level according to control performed by the control section 28, and outputs the direct current power to the resonance circuit 23.

The waveform generation circuit 22 detects a switching frequency set by the control section 28 and outputs a timing signal according to the switching frequency to the resonance circuit 23.

More specifically, the waveform generation circuit 22 is configured to have an oscillation source 22a and an oscillator 22b.

In the oscillation source 22a, (n+1) types of frequencies consisting of frequencies $f_0, f_1, f_2, \ldots, f_n$ are stored.

The oscillator 22b selects one frequency coinciding with the switching frequency set by the control section 28 from the (n+1) types of frequencies stored in the oscillation source 22a. The oscillator 22b then generates a timing signal according to the one frequency and outputs the timing signal to the resonance circuit 23.

The resonance circuit 23 has such a configuration as to be able to freely change its inductance value and capacitance value according to control performed by the control section 28. After the resonance circuit 23 has changed its inductance value and capacitance value according to control performed by the control section 28, it generates and outputs high frequency power on the basis of the direct current power outputted from the direct current power supply circuit 21 and the timing signal outputted from the waveform generation circuit 22. That is, high frequency power generated by the resonance circuit 23 has a signal level according to the direct current power outputted from the direct current power supply circuit 21 and having a frequency according to the timing signal outputted from the waveform generation circuit 22.

When a high frequency voltage having a predetermined frequency and a peak value V1 is applied to the primary-side circuit of the transformer 24, the transformer 24 generates in its secondary-side circuit a high frequency voltage having the predetermined frequency and a peak value V2 by electromagnetic induction. When the high frequency voltage having the predetermined frequency and a peak value V2 is generated in the secondary-side circuit of the transformer 24, a high frequency current based on this high frequency voltage and having the predetermined frequency and a peak value I2 is outputted to the treatment instrument 3 connected to the high frequency power supply 2 via the current sensor 25 and the cable 31. Also, when the high frequency voltage having the predetermined frequency and a peak value I2 is generated in the secondary-side circuit of the transformer 24, a high frequency voltage based on the high frequency current and having the predetermined frequency and a peak value V2 is outputted to the treatment instrument 3 connected to the high frequency power supply 2 via the voltage sensor 26 and the cable 31.

The voltage sensor 26 detects a value according to the peak value V2 of the high frequency voltage generated in the secondary-side circuit of the transformer 24 and outputs a value according to the detected peak value V2 as output voltage value information to the A/D converter 27.

The current sensor 25 detects a value according to the peak value I2 of the high frequency current generated based on the high frequency voltage in the secondary-side circuit of the transformer 24 and outputs a value according to the detected peak value I2 as output current value information to the A/D converter 27.

The A/D converter 27 converts each of the output voltage value information outputted from the voltage sensor 26 and the output current value information outputted from the current sensor 25 from analog form into digital form and outputs the converted information to the control section 28.

The control section 28 constituted by a CPU and other components continuously performs control for supplying high frequency power to the treatment instrument 3 while the command signal is being outputted from at least one of the hand switch 32 and the foot switch 4.

The control section 28 computes the impedance value Z of a living tissue in an objective portion on the basis of the digital data on the output voltage value information and the output current value information outputted from the A/D converter 27. When the control section 28 detects that the impedance value Z has exceeded a predetermined threshold value Zth, the control section 28 performs control for outputting high frequency power of a higher frequency on the waveform generation circuit 22 and the resonance circuit 23. Also, when the control section 28 detects that the impedance value Z is higher than predetermined threshold value Zth and the frequency of high frequency power outputted from the resonance circuit 23 is at the maximum, the control section 28 performs control for substantially stopping the output of high frequency power on the direct current power supply circuit 21, the waveform generation circuit 22 and the resonance circuit 23. The control section 28 in the present embodiment may also perform control for sounding a buzzer or the like (not shown) to inform an operator or the like that the output of high frequency power is substantially (or completely) stopped. A state where the output of high frequency power is substantially stopped means as a state where high frequency power having such a low level as not to cauterize a living tissue is being continuously outputted.

On the other hand, high frequency power (high frequency current and high frequency voltage) outputted from the high frequency power supply 2 is supplied to the treatment instrument 3 via the cable 31.

As shown in FIG. 1, the treatment instrument 3 is formed as a pair of forceps having two shanks connected so as to intersect with each other, and is configured to have the cable 31 extending from proximal end portions of the two shanks, the hand switch 32 electrically connected to the high frequency power supply 2 via a signal line, handles 33a and 33b respectively provided on the proximal end portions of the two shanks, and jaws 34a and 34b respectively provided on distal end portions of the two shanks. The treatment instrument 3 thus configured is capable of grasping a living tissue in an objective portion between the jaws 34a and 34b by operating the handles 33a and 33b so that the handles 33a and 33b are brought closer to each other.

High frequency power supplied to the treatment instrument 3 via the cable 31 is transmitted via conductors, not shown, respectively provided in the two shanks of the treatment instrument 3 in the lengthwise direction, and is thereafter outputted to the jaws 34a and 34b. When high frequency power is outputted to the jaws 34a and 34b in a state where a living tissue in an objective portion is grasped between the jaws 34a and 34b, the high frequency power is applied to the living tissue in the objective portion.

The operation of the electrosurgical apparatus 1 will now be described.

An operator brings the distal end portion of the treatment instrument 3 to a living tissue in an objective portion and holds the living tissue in the objective portion by grasping the living tissue between the jaws 34a and 34b by operating the handles 33a and 33b. In this state, the operator presses the hand switch 32 or the foot switch 4 to provide a command to output high frequency power from the high frequency power supply 2. With this operation, high frequency power is applied to the living tissue in the objective portion grasped between the jaws 34a and 34b.

As high frequency power is continuously applied to the living tissue in the objective portion, a phenomenon occurs in which, for example, as shown in FIGS. 2 and 3, at a moment close to a point in time at which a vapor layer is formed in the living tissue, the impedance value Z increases with time t, while the value of power W applied to the living tissue decreases with time t.

On the other hand, the control section 28 determines whether or not the impedance value Z exceeds the predetermined threshold value Zth by monitoring at desired times digital data on output voltage value information and output current value information outputted from the A/D converter 27 (step S1 in FIG. 5). The control section 28 maintains the application of high frequency power to the living tissue in the objective portion as long as the impedance value Z does not exceed the predetermined threshold value Zth. When the control section 28 detects that the impedance value Z has exceeded the predetermined threshold value Zth, the control section 28 determines whether or not the frequency f of high frequency power presently outputted is the upper limit value fmax (step S2 in FIG. 5). It is assumed that in the present embodiment the predetermined threshold value Zth is set in advance as a value between 400 Ω and 1000 Ω, and that the predetermined threshold value Zth is higher than the impedance at which a change from constant-power control to constant-voltage control is made.

When the control section 28 detects that the frequency f of high frequency power is not the upper limit value fmax (step S2 in FIG. 5), the control section 28 performs control for increasing the frequency f one step on the waveform generation circuit 22 and the resonance circuit 23 (step S3 in FIG. 5). By this control, for example, as shown in FIG. 4, the frequency f of high frequency power is increased stepwise, as shown by $f_0 \to f_1$, $f_1 \to f_2$, and $f_2 \to f_3$, at points in time (times t1, t2 and t3) at which the impedance value Z exceeds the predetermined threshold value Zth.

With consideration of an increase in electrical conductivity of the living tissue with the increase in frequency, for example, as shown in FIGS. 2 and 3, the impedance value Z of the living tissue in the objective portion decreases at the points in time (times t1, t2 and t3) at which the frequency f of high frequency power is increased, and, simultaneously, the value of power W applied to the living tissue again is again increased to a value substantially equal to the power value at the initial stage (immediately after the start of application of high frequency power to the living tissue in the objective portion). The correlation between the frequency and the electric conductivity of the living tissue is, for example, as shown in the graph of FIG. 6.

The control section 28 repeats performing the above-described control for increasing stepwise the frequency f of high frequency power each time the impedance value Z exceeds the predetermined threshold value Zth. When the control section 28 detects (in step S2 in FIG. 5), at time t4, that the impedance value Z has finally exceeded the predetermined threshold value Zth (step S1 in FIG. 5) and the frequency f of high frequency power is the upper limit value fmax (e.g., $f_3$ shown in FIG. 4), the control section 28 performs control for substantially stopping the output of high frequency power on the direct current power supply circuit 21, the waveform generation circuit 22 and the resonance circuit 23. The control section 28 in the present embodiment may also perform control for sounding a buzzer or the like (not shown) to inform the operator or the like that the output of high frequency power is substantially stopped. The control section 28 in the present embodiment is not limited to the one that substantially stops the output of high frequency power at time t4. For example, the control section 28 may completely stop the output of high frequency power.

The control section 28 in the present embodiment is assumed to perform control for increasing the frequency f of high frequency power stepwise in the range of about 350 kHz to 5 MHz for example.

Also, a control section which performs control for increasing the frequency f of high frequency power from one step to another in a plurality of steps may suffice as the control section 28 in the present embodiment. The control section 28 is not limited to the one that increases the frequency f of high frequency power in the four steps corresponding to $f_0$, $f_1$, $f_2$ and $f_3$.

Further, the control section 28 in the present embodiment is not limited to the one that performs control for increasing the frequency f of high frequency power one step when detecting that the impedance value Z has exceeded the predetermined threshold value. For example, the control section 28 may perform control for increasing the frequency f of high frequency power one step when detecting that the value of power W applied to a living tissue is smaller than half the initial power value. Also, the control section 28 in the present embodiment may perform control for increasing the frequency f of high frequency power one step on the basis of either of the output voltage value information and the output current value information. Also, the control section 28 in the present embodiment may perform control for increasing the frequency f one step when detecting that the gradient of the impedance value Z with respect to passage of time has exceeded a predetermined threshold value.

On the other band, the control section 28 in the present embodiment may perform control relating to high frequency induction heating for the purpose of obtaining an improved dehydration effect.

More specifically, the control section 28 in the present embodiment may further perform, in the sequential process shown in FIG. 5, control for outputting high frequency power having the frequency fmax for a predetermined time period after detecting that the impedance value Z has exceeded the predetermined threshold value Zth and the frequency f of high frequency power is the upper limit value fmax.

With consideration of the point that with the progress of dehydration a vapor layer is formed in a living tissue and the impedance of the living tissue increases, a situation can occur where the dehydration does not proceed further because the power applied to the living tissue decreases with the time.

Also, with consideration of the point that with the progress of dehydration a vapor layer is formed in a living tissue and the impedance of the living tissue increases, it is thought that the dehydrated state of the living tissue cannot be correctly detected by simply detecting the increase in impedance in the living tissue.

On the other hand, in the conventional art, the output power for example is only determined on the basis of the tissue impedance response in the very initial stage. Therefore, the conventional art has the problem that a living tissue in an objective portion is not sufficiently dehydrated and the joining strength in the objective portion is weak.

As described above, the electrosurgical apparatus 1 in the present embodiment is capable of continuously applying electric power of substantially the same value as that immediately after a start of application of high frequency power to a living tissue by increasing the frequency of the high frequency power stepwise with increase in impedance value of the living tissue. Consequently, the electrosurgical apparatus 1 in the present embodiment is capable of dehydrating a living tissue in an objective portion.

The present invention is not limited to each embodiment described above. Needless to say, various modifications and applications can be made without departing from the gist of the invention.

The invention claimed is:

1. An electrosurgical apparatus comprising:
a high frequency power generation section which generates high frequency power to be applied to a living tissue;
a voltage detection section which detects a voltage of the high frequency power;
a current detection section which detects a current of the high frequency power;
an impedance computation section which computes the impedance between holding members for grasping the living tissue, on the basis of the voltage and the current;
a detection section which detects that a value of the impedance computed by the impedance computation section exceeds a predetermined threshold value;
a waveform generation circuit which generates a timing signal according to a first frequency of the high frequency power to be generated from the high frequency power generation section or a timing signal according to a second frequency higher than the first frequency and outputs the generating timing signal; and
a control section which performs control for switching the timing signal to be outputted from the waveform generation circuit from the timing signal according to the first frequency to the timing signal according to the second frequency based on a result obtained by the detection section.

2. The electrosurgical apparatus according to claim 1, wherein when the control section detects that the impedance has exceeded the predetermined threshold value and the frequency is at the maximum, the control section performs control for stopping or substantially stopping output of the high frequency power on the high frequency power generation section.

3. The electrosurgical apparatus according to claim 1, wherein when the control section detects that the impedance has exceeded the predetermined threshold value and the frequency is at the maximum, the control section performs control for outputting high frequency power having the maximum frequency for a predetermined time period on the high frequency power generation section.

4. The electrosurgical apparatus according to claim 1, wherein when the impedance exceeds the predetermined threshold value, the control section performs control for increasing the frequency stepwise in the range from 350 kHz to 5 MHz on the high frequency power generation section.

5. A method of controlling an electrosurgical apparatus comprising:
a step of generating high frequency power to be applied to a living tissue by a high frequency power generation section;
a step of detecting a voltage of the high frequency power by a first detection section;
a step of detecting a current of the high frequency power by a second detection section;
a step of computing the impedance between holding members for grasping the living tissue, on the basis of the voltage and the current by an impedance computation section;
a step of detecting that a value of the impedance computed by the impedance computation section exceeds a predetermined threshold value by a third detection section;
a step of generating a timing signal according to a first frequency of the high frequency power to be generated from the high frequency power generation section or a timing signal according to a second frequency higher than the first frequency and outputting the generated timing signal by a waveform generation circuit; and
a step of switching the timing signal to be outputted from the waveform generation circuit from the timing signal according to the first frequency to the timing signal according to the second frequency based on a result obtained by a third detection section by control of a control section.

6. The method of controlling an electro surgical apparatus according to claim 5, further comprising a step of stopping or substantially stopping output of the high frequency power when a situation where the impedance has exceeded the predetermined threshold value and where the frequency is at the maximum value is detected.

7. The method of controlling an electro surgical apparatus according to claim 5, further comprising a step of outputting high frequency power having the maximum frequency for a predetermined time period when a situation where the impedance has exceeded the predetermined threshold value and where the frequency is at the maximum value is detected.

8. The method of controlling an electro surgical apparatus according to claim 5, wherein when the impedance exceeds the predetermined threshold value, the frequency is increased stepwise in the range from 350 kHz to 5 MHz.

9. An electrosurgical apparatus comprising:
high frequency power generation means which generates high frequency power to be applied to a living tissue;
voltage detection means which detects a voltage of the high frequency power;
current detection means which detects a current of the high frequency power;
impedance computation means which computes the impedance between holding members for grasping the living tissue, on the basis of the voltage and the current;
detection means which detects that a value of the impedance computed by the impedance computation means exceeds a predetermined threshold value;
waveform generation means which generates a timing signal according to a first frequency of the high frequency power to be generated from the high frequency power generation means or a timing signal according to a second frequency higher than the first frequency and outputs the generated timing signal; and
control means which performs control for switching the timing signal to be outputted from the waveform generation means from the timing signal according to the first frequency to the timing signal according to the second frequency based on a result obtained by the detection means.

10. The electrosurgical apparatus according to claim 1, wherein the frequency of the high frequency power generated from the high frequency power generation section is increased stepwise, when the value of the impedance exceeds the predetermined threshold value.

* * * * *